United States Patent
Csavoy et al.

(10) Patent No.: US 8,010,177 B2
(45) Date of Patent: Aug. 30, 2011

(54) INTRAOPERATIVE IMAGE REGISTRATION

(75) Inventors: Andrew N. Csavoy, Minneapolis, MN (US); Matthew S. Solar, Indialantic, FL (US); Jeffrey M. Waynik, Nederland, CO (US); Mark S. Freas, Palm Bay, FL (US); Thomas I. Miller, Palm Bay, FL (US); Keith Sootsman, Kalamazoo, MI (US)

(73) Assignee: Medtronic, Inc., Minneapolis, MN (US)

( * ) Notice: Subject to any disclaimer, the term of this patent is extended or adjusted under 35 U.S.C. 154(b) by 1162 days.

(21) Appl. No.: 11/739,513

(22) Filed: Apr. 24, 2007

(65) Prior Publication Data

US 2008/0269588 A1  Oct. 30, 2008

(51) Int. Cl.
*A61B 5/05* (2006.01)

(52) U.S. Cl. ........ 600/407; 600/424; 600/410; 600/429; 600/433; 606/130; 606/99; 606/104

(58) Field of Classification Search .................. 600/407, 600/410, 424, 429, 433; 606/61, 130, 86, 606/99, 104
See application file for complete search history.

(56) References Cited

U.S. PATENT DOCUMENTS

| | | | |
|---|---|---|---|
| 5,592,939 A | 1/1997 | Martinelli | |
| 5,740,808 A | 4/1998 | Panescu et al. | |
| 5,913,820 A | 6/1999 | Bladen et al. | |
| 5,983,126 A | 11/1999 | Wittkampf et al. | |
| 6,381,485 B1 | 4/2002 | Hunter et al. | |
| 6,474,341 B1 | 11/2002 | Hunter et al. | |
| 6,482,182 B1 | 11/2002 | Carroll et al. | |
| 6,484,049 B1 | 11/2002 | Seeley et al. | |
| 6,493,573 B1 | 12/2002 | Martinelli et al. | |
| 6,516,212 B1 | 2/2003 | Bladen et al. | |
| 2002/0035321 A1 | 3/2002 | Bucholz et al. | |
| 2003/0114752 A1 | 6/2003 | Henderson et al. | |
| 2005/0049486 A1 | 3/2005 | Urquhart et al. | |
| 2005/0085714 A1 | 4/2005 | Foley et al. | |
| 2005/0085720 A1 | 4/2005 | Jascob et al. | |

FOREIGN PATENT DOCUMENTS

WO  WO-2005013841  2/2005

OTHER PUBLICATIONS

International Search Report for PCT/US2007/009924 completed on Jan. 14, 2008 and mailed on Jan. 24, 2008.
Written Opinion of the International Searching Authority for PCT/US2007/009924 mailed on Jan. 24, 2008.

*Primary Examiner* — Brian Casler
*Assistant Examiner* — Joel M Lamprecht
(74) *Attorney, Agent, or Firm* — Scott A. Marks; Harness, Dickey & Pierce, P.L.C.

(57) ABSTRACT

A system to allow registration of a patient to image space is disclosed. The registration can be performed without touching a plurality of fiducial points on the patient or in the image data. The registration process can eliminate manual steps of image to patient registration and image to image registration.

38 Claims, 4 Drawing Sheets

INTRAOPERATIVE IMAGE REGISTRATION

FIELD

The present disclosure relates to a surgical navigation system, and particularly to a system for intraoperative registration of image data.

BACKGROUND

The statements in this section merely provide background information related to the present disclosure and may not constitute prior art.

In an anatomy, such as a human anatomy, various anatomical portions and functions maybe damaged or require repair after a period of time. The anatomical portion or function maybe injured due to wear, aging, disease, or exterior trauma. To assist the patient, a procedure may be performed that may require access to an internal region of the patient through an incision. Due to exterior soft tissue, visualization of portions of the interior of the anatomy maybe difficult or require a large opening in the patient.

Image data maybe required of a patient to assist in planning, performing, and post-operative analysis of a procedure. For example, magnetic resonance or computer tomography image data can be acquired of the patient to assist in diagnosing and planning a procedure. The image data acquired of the patient can also be used to assist in navigating various instruments relative to the patient while performing a procedure.

It is known to fixedly interconnect fiducial markers with a patient while imaging the patient. The fiducial markers are then identified or found on the patient with an instrument operated by a user. In the image data the position of the correlating fiducial marker is also identified by the user. It is desirable, therefore, to reduce manual tasks of the user. It is also desirable to provide a system that allows for registration of the image space to the patient space without requiring a user to touch or contact one or more fiducial markers on a patient.

SUMMARY

During a surgical procedure on an anatomy, such as a human anatomy, instruments, implants, prostheses, leads, and the like can be positioned in the anatomy. The various instruments or devices are generally positioned through incisions formed in hard tissue and/or soft tissue, such as the dermis or skull, of the anatomy. Therefore, anatomy of the patient can obscure or limit visualization of the devices in the anatomy during the procedure. It may be desirable, therefore, to provide a mechanism to determine a position of the instruments within the anatomy.

According to various embodiments a navigation system for registering an image space to a physical space relative to a patient for a surgical procedure is taught. The system can include a tracking system including a localizer and a tracking device. The system can also include an intraoperative imaging system that can acquire intraoperative image data of the patient. The system can further include a processor operable to at least one of determine a position of the tracking device in the physical space, determine an intraoperative fiducial point in the intraoperative image data, determine a preoperative image data fiducial point in a preoperative image data, correlate the intraoperative image data and the preoperative image data with the intraoperative image data fiducial point and the preoperative image data fiducial point, or combinations thereof. The preoperative image data can be registered to the physical space based upon the intraoperative image data.

According to various embodiments a method of registering image space to physical space relative to a patient is taught. The method can include acquiring preoperative image data of the patient and determining a preoperative image data fiducial point in the preoperative image data. The method can also include acquiring intraoperative image data and determining an intraoperative image data fiducial point in the intraoperative image data. The preoperative image data and the intraoperative image data can be correlated using the determined preoperative image data fiducial point in the preoperative image data, the determined an intraoperative image data fiducial point in the intraoperative image data, or combinations thereof. Also, the preoperative image data can be correlated to the physical space.

According to various embodiments a method of registering image space to physical space relative to a patient is taught. The method can include accessing a first image data set of the patient and determining a first image data set fiducial point. The patient can be prepared for a surgical procedure in at least a portion of the physical space. The method can also include defining at least a portion of the physical space in a second image data set of the patient and determining a second image data set fiducial point. The first image data set can be correlated to the second image data set at least in part by matching the first image data set fiducial point and the second image data set fiducial point. Also, the first image data set can be registered with the physical space with the correlation of the image data set and the second image data set.

Further areas of applicability will become apparent from the description provided herein. It should be understood that the description and specific examples are intended for purposes of illustration only and are not intended to limit the scope of the present disclosure.

DRAWINGS

The drawings described herein are for illustration purposes only and are not intended to limit the scope of the present disclosure in any way.

DETAILED DESCRIPTION

Figure 1:
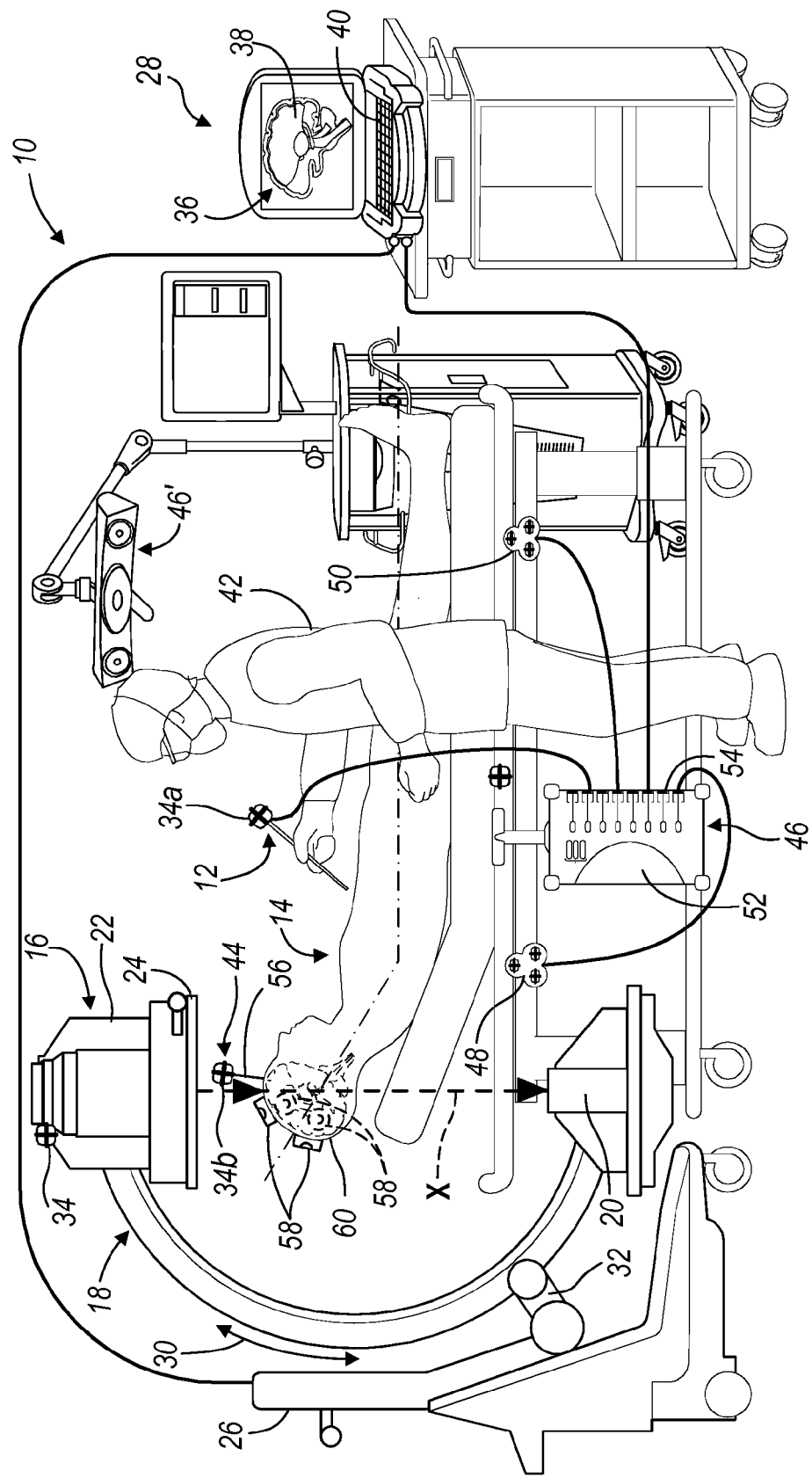
FIG. 1 is an environmental view of a surgical navigation system or computer aided surgical system, according to various embodiments.

The following description is merely exemplary in nature and is not intended to limit the present disclosure, application, or uses. Although the following description illustrates and describes a procedure relative to a cranium of a patient, the current disclosure is not to be understood to be limited to such a procedure. For example, a procedure can also be performed relative to a spinal column, heart, vascular system, etc. Therefore, discussion herein relating to a specific region of the anatomy will be understood to be applicable to all regions of the anatomy, unless specifically described otherwise.

As discussed herein, various systems and elements can be used to assist in a surgical procedure. For example, image data can be acquired of a patient to assist in illustrating the location of an instrument relative to a patient. Generally, image space can be registered to physical space, in general, and particularly to patient space to assist in the display and navigation of a procedure. Fiducial markers can be affixed to the patient during imaging and registration. Alternatively, a fiducial marker-less system can be used. Fiducial marker-less systems can use other techniques, including surface or contour matching, as discussed herein. One skilled in the art will understand, however, that having present fiducial markers when performing a fiducial marker-less procedure can be possible.

A surgical procedure can be planned and prepared for at least in part by obtaining image data of a patient for use in planning a procedure. The image data of the patient can include any appropriate image data, including magnetic resonance image data, computed tomography image data, ultrasound image data, or any appropriate image data. The image data obtained of the patient can be acquired at any appropriate time prior to a procedure. For example, magnetic resonance image data can be acquired of the patient hours or days prior to a procedure. The procedure can be planned based on the image data acquired of the patient. For example, a trajectory of an implant can be planned, a final location of an implant can be planned, or any appropriate planning can occur. The image data relative to which planning occurs can then be used during the surgical procedure to assist in navigating the procedure, such as the implants, or other portions or instruments relative to the patient. The navigation can ensure that the appropriate therapy occurs, such as an appropriate or planned trajectory, final placement of implant, or the like. Nevertheless, image data acquired of the patient prior to a surgical procedure can be registered, as discussed herein, to the patient or patient space.

Registration of the image data defining image space to the patient space can be performed, according to various embodiments. For example, image data can be acquired of the patient intraoperatively, generally after the acquisition of the preoperative image data, and the intraoperative image data can be used to register the patient space to the preoperative image space. The preoperative image space, relative to which various planning and determination steps have occurred, can be registered to the patient space intraoperatively using image data acquired of the patient during the operative procedure or immediately preceding the operative procedure. For example, as discussed further herein, a patient can be prepared for a surgery by positioning the patient in an operating room and acquiring image data of the patient. The intraoperative image data, therefore, can occur or be acquired before an incision of the patient has occurred, but after the patient is at least partially prepped for a procedure. Moreover, as discussed further herein, any appropriate intraoperative image data can be acquired. The type of intraoperative image data acquired of the patient can be appropriate to the type of procedure being performed, similar to the preoperative image data, or any appropriate type of image data.

Generally, an operating theatre can include a navigation system 10, as illustrated in FIG. 1. The navigation system 10 that can be used for various procedures. The navigation system 10 can be used to track the location of a device 12, such as a pointer probe, relative to a patient 14 to assist in the implementation or performance of a surgical procedure. It should be further noted that the navigation system 10 may be used to navigate or track other devices including: catheters, probes, needles, leads, implants, etc. According to various embodiments, examples include ablation catheters, deep brain stimulation (DBS) leads or electrodes, micro-electrode (ME) or leads for recording, etc. Moreover, the navigated device may be used in any region of the body. The navigation system 10 and the various devices may be used in any appropriate procedure, such as one that is generally minimally invasive, arthroscopic, percutaneous, stereotactic, or an open procedure. Therefore, devices that can be tracked include instruments for performing a therapy, devices for use in registration, dynamic references frames (DRF) for tracking the patient, etc.

Although an exemplary navigation system 10 including an imaging system 16 are discussed herein, one skilled in the art will understand that the disclosure is merely for clarity of the present discussion and any appropriate imaging system, navigation system, patient specific data, and non-patient specific data can be used. For example, the intraoperative imaging system can include an O-arm® imaging system (FIG. 2) sold by Breakaway Imaging, LLC. having a place of business in Massachusetts, USA. or an MRI imaging system, such as the PoleStar® MRI sold by Medtronic, Inc. (FIG. 3). It will be understood that the navigation system 10 can incorporate or be used with any appropriate preoperatively or intraoperatively acquired image data.

The navigation system 10 can include the optional imaging device 16 that is used to acquire pre-, intra-, or post-operative, including real-time, image data of the patient 14. In addition, data from atlas models can be used to produce morphed images for navigation. The morphed images or morphed image data is not pure image data of the patient and includes information from the atlas model. Also, atlas models can be morphed or changed based upon patient specific information. Also, substantially imageless systems can be used, such as those disclosed in U.S. patent application Ser. No. 10/687, 539, filed Oct. 16, 2003, now U.S. Pat. App. Pub. No. 2005/0085714, entitled "METHOD AND APPARATUS FOR SURGICAL NAVIGATION OF A MULTIPLE PIECE CONSTRUCT FOR IMPLANTATION", incorporated herein by reference. Various systems can use data based on determination of the position of various elements represented by geometric shapes.

The optional imaging device 16 is, for example, a fluoroscopic X-ray imaging device that may be configured as a C-arm 18 having an X-ray source 20, an X-ray receiving section 22, an optional calibration and tracking target 24 and optional radiation sensors. The calibration and tracking target 24 includes calibration markers (not illustrated). Image data may also be acquired using other imaging devices, such as those discussed above and herein.

An optional imaging device controller 26 may control the imaging device 16, such as the C-arm 18, which can capture the X-ray images received at the receiving section 22 and store the images for later use. The controller 26 may also be separate from the C-arm 18 and can be part of or incorporated into a work station 28. The controller 26 can control the rotation of the C-arm 18. For example, the C-arm 18 can move in the direction of arrow 30 or rotate about a longitudinal axis 14a of the patient 14, allowing anterior or lateral views of the patient 14 to be imaged. Each of these movements involves rotation about a mechanical axis 32 of the C-arm 18. The movements of the imaging device 16, such as the C-arm 18 can be tracked with a tracking device 34. As discussed herein, the tracking device, according to various embodiments, can be any appropriate tracking device to work with any appropriate tracking system (e.g. optical, electromagnetic, acoustic, etc.). Therefore, unless specifically discussed otherwise, the tracking device can be any appropriate tracking device.

In the example of FIG. 1, the longitudinal axis 14a of the patient 14 is substantially in line with the mechanical axis 32 of the C-arm 18. This enables the C-arm 18 to be rotated relative to the patient 14, allowing images of the patient 14 to be taken from multiple directions or in multiple planes. An example of a fluoroscopic C-arm X-ray device that may be used as the optional imaging device 16 is the "Series 9600 Mobile Digital Imaging System," from GE Healthcare, (formerly OEC Medical Systems, Inc.) of Salt Lake City, Utah. Other exemplary fluoroscopes include bi-plane fluoroscopic systems, ceiling mounted fluoroscopic systems, cath-lab fluoroscopic systems, fixed C-arm fluoroscopic systems, isocentric C-arm fluoroscopic systems, three-dimensional (3D) fluoroscopic systems, intraoperative O-arm™ imaging systems, etc.

The C-arm imaging system 18 can be any appropriate system, such as a digital or CCD camera, which are well understood in the art. Two dimensional fluoroscopic images that may be taken by the imaging device 16 are captured and stored in the C-arm controller 26. Multiple two-dimensional images taken by the imaging device 16 may also be captured and assembled to provide a larger view or image of a whole region of the patient 14, as opposed to being directed to only a portion of a region of the patient. For example, multiple image data or sets of data of a patient's leg, cranium, and brain may be appended together to provide a full view or complete set of image data of the leg or brain that can be later used to follow contrast agent, such as bolus or therapy tracking. The multiple image data can include multiple two-dimensional (2D) slices that are assembled into a 3D model or image.

The image data can then be forwarded from the C-arm controller 26 to the navigation computer and/or processor controller or work station 28 having a display device 36 to display image data 38 and a user interface 40. The work station 28 can also include or be connected to an image processor, a navigation processor, and a memory to hold instruction and data. The work station 28 can also include an optimization processor that assists in a navigated procedure. It will also be understood that the image data is not necessarily first retained in the controller 26, but may also be directly transmitted to the workstation 28. Moreover, processing for the navigation system and optimization can all be done with a single or multiple processors all of which may or may not be included in the workstation 28.

The work station 28 provides facilities for displaying the image data 38 as an image on the display device 36, saving, digitally manipulating, or printing a hard copy image of the received image data. The user interface 40, which may be a keyboard, mouse, touch pen, touch screen or other suitable device, allows a physician or user 42 to provide inputs to control the imaging device 16, via the C-arm controller 26, or adjust the display settings of the display 36. The work station 28 may also direct the C-arm controller 26 to adjust the rotational axis 32 of the C-arm 18 to obtain various two-dimensional images in different planes in order to generate representative two-dimensional and three-dimensional images.

While the optional imaging device 16 is shown in FIG. 1, any other alternative 2D, 3D or 4D imaging modality may also be used. For example, any 2D, 3D or 4D imaging device, such as isocentric fluoroscopy, bi-plane fluoroscopy, ultrasound, computed tomography (CT), multi-slice computed tomography (MSCT), magnetic resonance imaging (MRI), positron emission tomography (PET), optical coherence tomography (OCT) (a more detailed discussion on optical coherence tomography (OCT), is set forth in U.S. Pat. No. 5,740,808, issued Apr. 21, 1998, entitled "Systems And Methods For Guiding Diagnostic Or Therapeutic Devices In Interior Tissue Regions" which is hereby incorporated by reference). Intra-vascular ultrasound (IVUS), intra-operative CT, single photo emission computed tomography (SPECT), planar gamma scintigraphy (PGS). Addition imaging systems include intraoperative MRI systems such as the PoleStar® MRI system sold by Medtronic, Inc. Further systems include the O-Arm® imaging system sold by Breakaway Imaging, LLC. The images may also be obtained and displayed in two, three or four dimensions. In more advanced forms, four-dimensional surface rendering regions of the body may also be achieved by incorporating patient data or other data from an atlas or anatomical model map or from pre-operative image data captured by MRI, CT, or echocardiography modalities.

Image datasets from hybrid modalities, such as positron emission tomography (PET) combined with CT, or single photon emission computer tomography (SPECT) combined with CT, could also provide functional image data superimposed onto anatomical data to be used to confidently reach target sights within the patient 14. It should further be noted that the optional imaging device 16, as shown in FIG. 1, provides a virtual bi-plane image using a single-head C-arm fluoroscope as the optional imaging device 16 by simply rotating the C-arm 18 about at least two planes, which could be orthogonal planes to generate two-dimensional images that can be converted to three-dimensional volumetric images. By acquiring image data in more than one plane, an icon representing the location of an impacter, stylet, reamer driver, taps, drill, DBS, MEs for recording, probe, or other instrument, introduced and advanced in the patient 14, may be superimposed in more than one view on display 36 allowing simulated bi-plane or even multi-plane views, including two and three-dimensional views.

Four-dimensional (4D) image information can be used with the navigation system 10 as well. For example, the user 42 can use a physiologic signal, which can include Heart Rate (measured with an EKG), Breath Rate (Breath Gating) and combine this data with image data 38 acquired during the phases of the physiologic signal to represent the anatomy of the patient 14 at various stages of the physiologic cycle. For example, with each heartbeat the brain pulses (and therefore moves). Images can be acquired to create a 4D map of the brain, onto which atlas data and representations of a device, such as a surgical instrument can be projected. This 4D data set can be matched and co-registered with the physiologic signal (e.g. EKG) to represent a compensated image within the system. The image data registered with the 4D information can show the brain (or anatomy of interest) moving during the cardiac or breath cycle. This movement can be displayed on the display 36 as the image data 38. Also, the gating techniques can be used to eliminate movement in the image displayed on the display device 36.

Likewise, other imaging modalities can be used to gather the 4D dataset to which pre-operative 2D and 3D data can be matched. One need not necessarily acquire multiple 2D or 3D images during the physiologic cycle of interest (breath or heart beat). Ultrasound imaging or other 4D imaging modalities can be used to create an image data that allows for a singular static pre-operative image to be matched via image-fusion techniques and/or matching algorithms that are non-linear to match the distortion of anatomy based on the movements during the physiologic cycle. The combination of a dynamic reference frame 44 and 4D registration techniques can help compensate for anatomic distortions during movements of the anatomy associated with normal physiologic processes.

With continuing reference to FIG. 1, the navigation system 10 can further include a tracking system, such as, but not limited to, an electromagnetic (EM) tracking system 46 or an optical tracking system 46'. Either or both can be used alone or together in the navigation system 10. Moreover, discussion of the EM tracking system 46 can be understood to relate to any appropriate tracking system. Exemplary EM tracking systems include the AxiEM™, sold by Medtronic Navigation of Louisville, Colo. The optical tracking system 46' can include the StealthStation® Treon® and the StealthStation® Tria® both sold by Medtronic Navigation, Inc. Other tracking systems include acoustic, radiation, radar, infrared, etc.

The EM tracking system 46 can include a localizer, such as a coil array 48 and/or second coil array 50, a coil array controller 52, a navigation probe interface 54, a device 12 (e.g. catheter, needle, pointer probe, or instruments, as discussed herein) and the dynamic reference frame 44. An instrument tracking device 34a can also be associated with, such as fixed to, the instrument 12 or a guiding device for an instrument. The dynamic reference frame 44 can include a dynamic reference frame holder 56 and a removable tracking device 34b. Alternatively, the dynamic reference frame 44 can include the tracking device 34b that can be formed integrally or separately from the DRF holder 56.

Moreover, the DRF 44 can be provided as separate pieces and can be positioned at any appropriate position on the anatomy. For example, the tracking device 34b of the DRF can be fixed to the skin of the patient 14 with an adhesive. Also, the DRF 44 can be positioned near a leg, arm, etc. of the patient 14. Thus, the DRF 44 does not need to be provided with a head frame or require any specific base or holding portion.

The tracking devices 34, 34a, 34b or any tracking device as discussed herein, can include a sensor, a transmitter, or combinations thereof. Further, the tracking devices can be wired or wireless to provide a signal emitter or receiver within the navigation system. For example, the tracking device can include an electromagnetic coil to sense a field produced by the localizing array 48, 50 or reflectors that can reflect a signal to be received by the optical tracking system 46'. Nevertheless, one will understand that the tracking device can receive a signal, transmit a signal, or combinations thereof to provide information to the navigation system 10 to determine a location of the tracking device 34, 34a, 34b. The navigation system 10 can then determine a position of the instrument or tracking device to allow for navigation relative to the patient and patient space.

The coil arrays 48, 50 may also be supplemented or replaced with a mobile localizer. The mobile localizer may be one such as that described in U.S. patent application Ser. No. 10/941,782, filed Sept. 15, 2004, now U.S. Pat. App. Pub. No. 2005/0085720, entitled "METHOD AND APPARATUS FOR SURGICAL NAVIGATION", herein incorporated by reference. As is understood the localizer array can transmit signals that are received by the tracking devices 34, 34a, 34b. The tracking devices 34, 34a, 34b can then transmit or receive signals based upon the transmitted or received signals from or to the array 48, 50.

Further included in the navigation system 10 may be an isolator circuit or assembly (not illustrated separately). The isolator circuit or assembly may be included in a transmission line to interrupt a line carrying a signal or a voltage to the navigation probe interface 54. Alternatively, the isolator circuit included in the isolator box may be included in the navigation probe interface 80, the device 12, the dynamic reference frame 44, the transmission lines coupling the devices, or any other appropriate location. The isolator assembly is operable to isolate any of the instruments or patient coincidence instruments or portions that are in contact with the patient should an undesirable electrical surge or voltage take place.

It should further be noted that the entire tracking system 46, 46' or parts of the tracking system 46, 46' may be incorporated into the imaging device 16, including the work station 28. Incorporating the tracking system 46, 46' may provide an integrated imaging and tracking system. This can be particularly useful in creating a fiducial-less system. Moreover, fiducial marker-less systems can include a tracking device and a contour determining system, including those discussed herein. Any combination of these components may also be incorporated into the imaging system 16, which again can include a fluoroscopic C-arm imaging device or any other appropriate imaging device.

The EM tracking system 46 uses the coil arrays 48, 50 to create an electromagnetic field used for navigation. The coil arrays 48, 50 can include a plurality of coils that are each operable to generate distinct electromagnetic fields into the navigation region of the patient 14, which is sometimes referred to as patient space. Representative electromagnetic systems are set forth in U.S. Pat. No. 5,913,820, entitled "Position Location System," issued Jun. 22, 1999 and U.S. Pat. No. 5,592,939, entitled "Method and System for Navigating a Catheter Probe," issued Jan. 14, 1997, each of which are hereby incorporated by reference.

The coil array 48 is controlled or driven by the coil array controller 52. The coil array controller 52 drives each coil in the coil array 48 in a time division multiplex or a frequency division multiplex manner. In this regard, each coil may be driven separately at a distinct time or all of the coils may be driven simultaneously with each being driven by a different frequency.

Upon driving the coils in the coil array 48 with the coil array controller 52, electromagnetic fields are generated within the patient 14 in the area where the medical procedure is being performed, which is again sometimes referred to as patient space. The electromagnetic fields generated in the patient space induce currents in the tracking device 34, 34a, 34b positioned on or in the device 12, DRF 44, etc. These induced signals from the tracking devices 34, 34a, 34b are delivered to the navigation probe interface 54 and subsequently forwarded to the coil array controller 52. The navigation probe interface 54 can also include amplifiers, filters and buffers to directly interface with the tracking device 34b attached to the device 12. Alternatively, the tracking device 34b, or any other appropriate portion, may employ a wireless communications channel, such as that disclosed in U.S. Pat. No. 6,474,341, entitled "Surgical Communication Power System," issued Nov. 5, 2002, herein incorporated by reference, as opposed to being coupled directly to the navigation probe interface 54.

Various portions of the navigation system 10, such as the device 12, the dynamic reference frame 44, are equipped with at least one, and generally multiple, EM or other tracking devices 34a, 34b, that may also be referred to as localization sensors. The EM tracking devices 34a, 34b can include one or more coils that are operable with the EM localizer arrays 48, 50. An alternative tracking device may include an optical device, and may be used in addition to or in place of the electromagnetic tracking devices 34a, 34b. The optical tracking device may work with the optional optical tracking system 46'. One skilled in the art will understand, however, that any appropriate tracking device can be used in the navigation system 10. An additional representative alternative localization and tracking system is set forth in U.S. Pat. No. 5,983, 126, entitled "Catheter Location System and Method," issued Nov. 9, 1999, which is hereby incorporated by reference. Alternatively, the localization system may be a hybrid system that includes components from various systems.

In brief, the EM tracking device 34*a* on the device 12 can be in a handle or inserter that interconnects with an attachment and may assist in placing an implant or in driving a member. The device 12 can include a graspable or manipulable portion at a proximal end and the tracking device 34*b* may be fixed near the manipulable portion of the device 12 or at a distal working end, as discussed herein. The tracking device 34*a* can include an electromagnetic tracking sensor to sense the electromagnetic field generated by the coil array 48, 50 that can induce a current in the electromagnetic device 34*a*. Alternatively, the tracking device 34*a* can be driven (i.e., like the coil array above) and the tracking array 48, 50 can receive a signal produced by the tracking device 34*a*.

The dynamic reference frame 44 may be fixed to the patient 14 adjacent to the region being navigated so that any movement of the patient 14 is detected as relative motion between the coil array 48, 50 and the dynamic reference frame 44. The dynamic reference frame 44 can be interconnected with the patient in any appropriate manner, including those discussed herein. Relative motion is forwarded to the coil array controller 52, which updates registration correlation and maintains accurate navigation, further discussed herein. The dynamic reference frame 44 may include any appropriate tracking device. Therefore, the dynamic reference frame 44 may also be EM, optical, acoustic, etc. If the dynamic reference frame 44 is electromagnetic, it can be configured as a pair of orthogonally oriented coils, each having the same center or may be configured in any other non-coaxial or co-axial coil configurations.

Briefly, the navigation system 10 operates as follows. The navigation system 10 creates a translation map between all points in the image data generated from the imaging device 16 which can include external and internal portions, and the corresponding points in the patient's anatomy in patient space. After this map is established, whenever the tracked device 12 is used, the work station 36 in combination with the coil array controller 52 uses the translation map to identify the corresponding point on the image data or atlas model, which is displayed on display 36. This identification is known as navigation or localization. An icon representing the localized point or instruments is shown on the display 36 within several two-dimensional image planes, as well as on three and four dimensional images and models.

To enable navigation, the navigation system 10 must be able to detect both the position of the patient's anatomy and the position of the instrument 12 or an attachment member (e.g. tracking device 34*a*) attached to the instrument 12. Knowing the location of these two items allows the navigation system 10 to compute and display the position of the instrument 12 or any portion thereof in relation to the patient 14. The tracking system 46 is employed to track the instrument 12 and the anatomy of the patient 14 simultaneously.

The tracking system 46, if it is using an electromagnetic tracking assembly, essentially works by positioning the coil array 48, 50 adjacent to the patient 14 to generate a magnetic field, which can be low energy, and generally referred to as a navigation field. Because every point in the navigation field or patient space is associated with a unique field strength, the electromagnetic tracking system 46 can determine the position of the instrument 12 by measuring the field strength at the tracking device 34*a* location. The dynamic reference frame 44 is fixed to the patient 14 to identify the location of the patient in the navigation field. The electromagnetic tracking system 46 continuously computes or calculates the relative position of the dynamic reference frame 44 and the instrument 12 during localization and relates this spatial information to patient registration data to enable navigation of the device 12 within and/or relative to the patient 14. Navigation can include image guidance or imageless guidance.

Very briefly, and discussed further herein in various embodiments, patient registration is the process of determining how to correlate the position of the instrument 12 relative to the patient 14 to the position on the diagnostic or image data. To register the patient 14 or patient space to image space, one or more particular points from the image data can be selected and stored and then corresponding points on the anatomy of the patient can be determined. The selection of the points in the image space and on the patient 14 can be determined or selected according to various techniques, as discussed herein. The navigation system 10 analyzes the relationship between the two sets of points that are selected and computes a match, which correlates every point in the image data with its corresponding point on the patient's anatomy or the patient space.

The points that are selected to perform registration can be image fiducial points. The image fiducial points can be produced by a fiducial marker 58 imaged with the patient 14 or selected landmarks, such as anatomical landmarks. The landmarks or fiducial markers 58 are identifiable in the image data and identifiable and accessible on the patient 14. The anatomical landmarks can include individual or distinct points on the patient 14 or contours (e.g. three-dimensional contours) defined by the patient 14. The fiducial markers 58 can be artificial markers that are positioned on the patient 14. The artificial landmarks, such as the fiducial markers 58, can also form part of the dynamic reference frame 44, such as those disclosed in U.S. Pat. No. 6,381,485, entitled "Registration of Human Anatomy Integrated for Electromagnetic Localization," issued Apr. 30, 2002, herein incorporated by reference. Various fiducial marker-less systems, including those discussed herein, may not include the fiducial markers 58, or other artificial markers. The fiducial marker-less systems include a device or system to define in the physical space the landmark or fiducial points on the patient or contour on the patient. A fiducial marker-less system can include those that do not include artificial or separate fiducial markers that are attached to or positioned on the patient 14.

As discussed above, registration of the patient space or physical space to the image data or image space can require the correlation or matching of physical or virtual fiducial points and image fiducial points. The physical fiducial points can be the fiducial markers 58 or landmarks (e.g. anatomical landmarks) in the substantially fiducial marker-less systems.

The physical fiducial points and the image fiducial points in the image data 54 can be determined to allow for registration. As discussed herein, the determination of the various points can be based on a determination according to selected algorithms processed by a processor, user selection, combinations thereof, etc. The image fiducial points can be produced in the image data by the fiducial markers 48, particular landmarks, a contour (e.g. a 3D contour) of the patient 14 during acquisition of the image data, etc.

Once the physical fiducial points and the image fiducial points have been identified, the image space and the physical space can be registered. A processor, such as a processor within the workstation 28, can determine registration of the patient space to the image space. The registration can be performed according to generally known mapping or translation techniques. The registration can allow a navigated procedure using the image data.

With continuing reference to FIG. 1, an X-ray beam X can be emitted from the X-ray emitting section 20 and received in the imaging section 22. The X-ray beam X, as understood by one skilled in the art, can generally follow the path X that is known from the emitting section 20 to the imaging section 22. The X-ray beam path X followed by the X-ray can generally be predicted and is well understood, therefore, the image produced by the data acquired in the imaging section 22 can also be substantially understood by the position of the imaging section 22 relative to the imaging section 20. Moreover, as discussed above, the position of the imaging section 22 can be determined with the tracking device 34. Therefore, the image data produced with the imaging section 22 can be correlated to a substantially precise location in physical space relative to the patient 14.

Also as discussed above, the fiducial markers 58 can be included on the patient 14. The fiducial markers 58 can also be imaged if they are within the path of the X-ray beam X when image data is acquired. Therefore, the fiducial markers 58 can also be imaged as image data fiducial points in the image data acquired intraoperatively with the C-Arm 18. The fiducial markers 58 can be substantially precisely with the device 12 and the position of the C-arm can be determined with the tracking device 34 associated with the imaging section 22. The two positions can be correlated to determine the position of the C-arm 18 to the patient during the image data acquisition.

Figure 2:
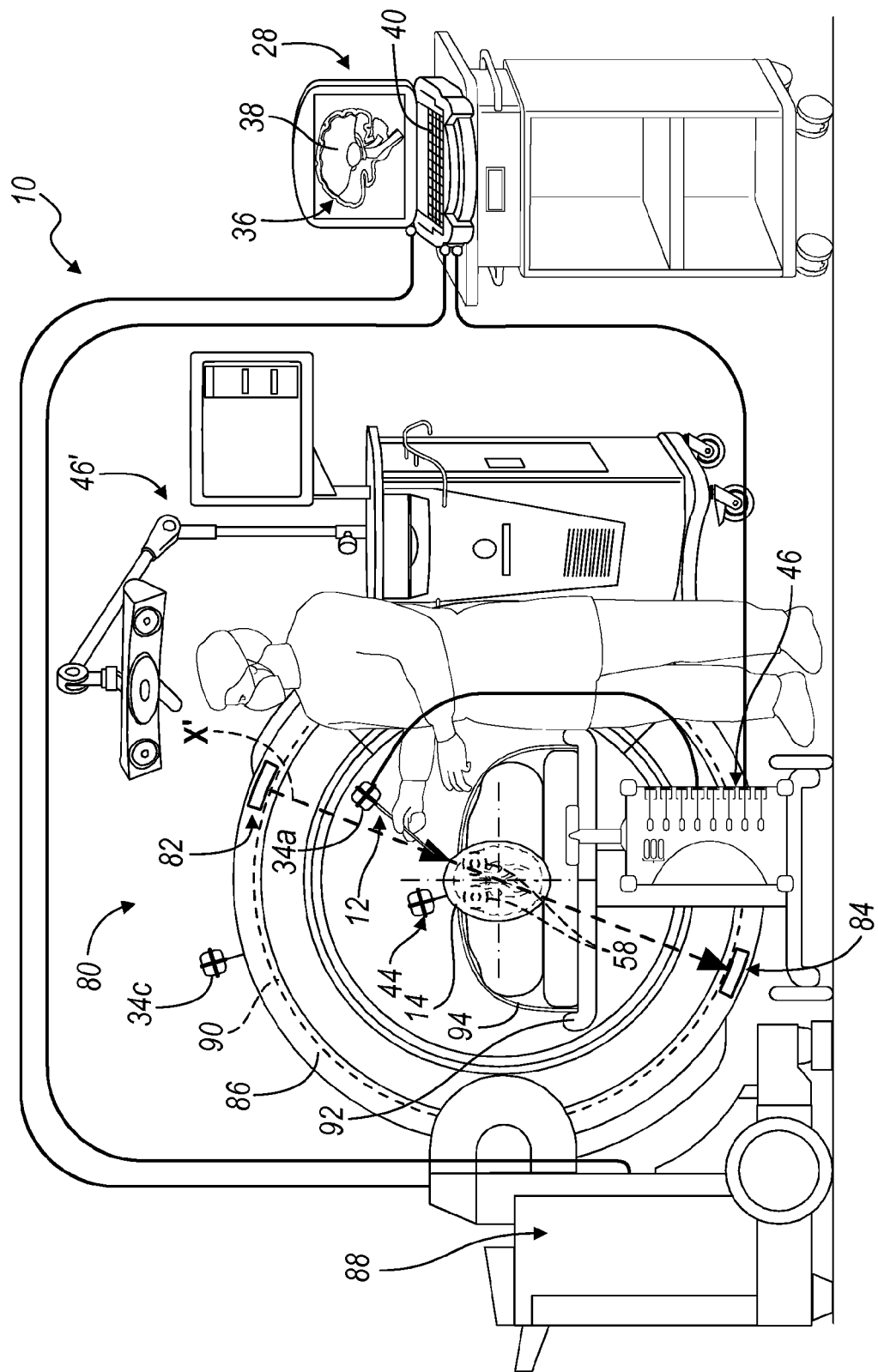
FIG. 2 is an environmental view of a surgical navigation system or computer aided surgical system, according to various embodiments.
Figure 3:
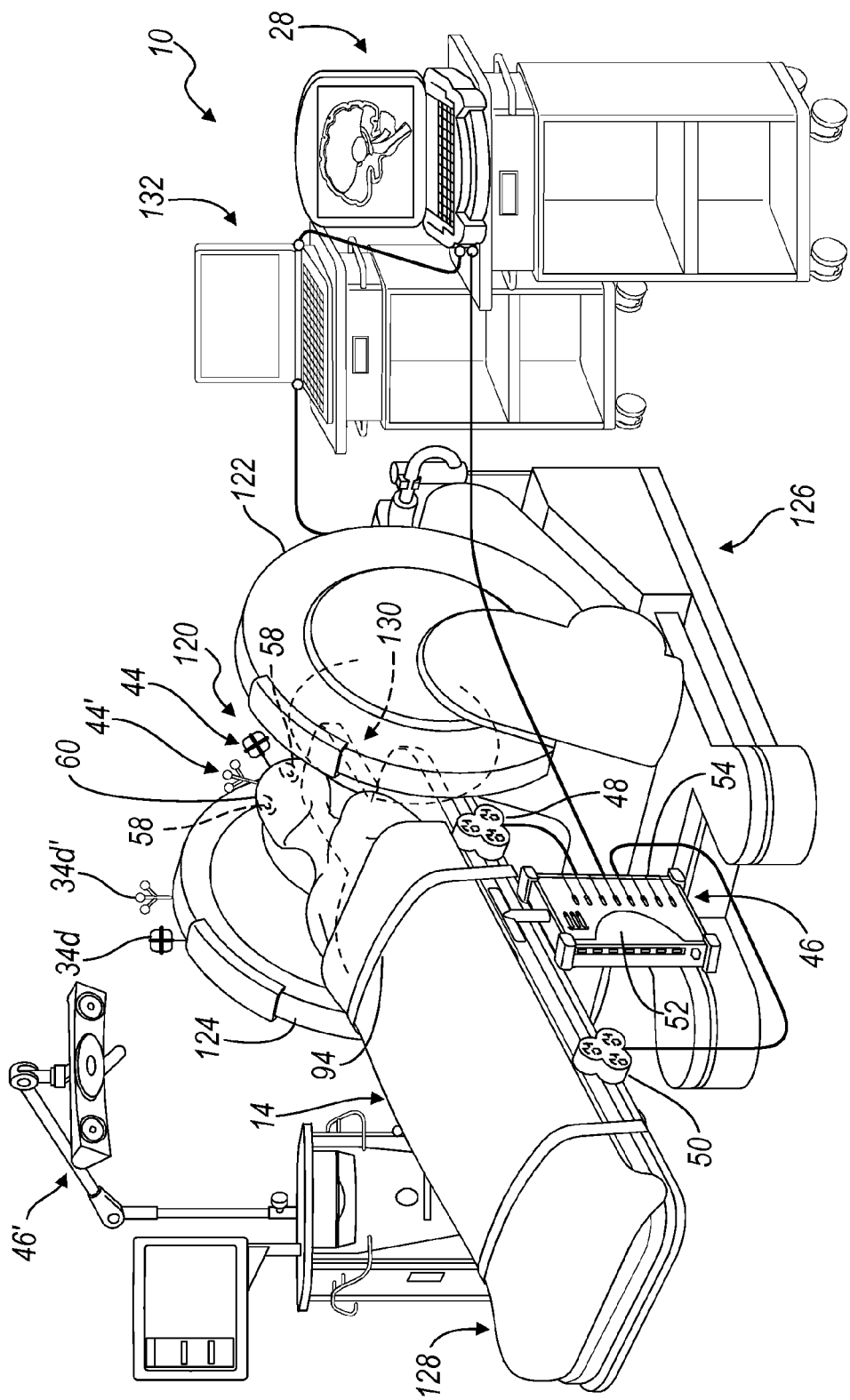
FIG. 3 is an environmental view of a surgical navigation system or computer aided surgical system, according to various embodiments.

With reference to FIG. 2, the navigation system 10 can include, as the optional intraoperative imaging system 16, an O-Arm® imaging system 80 (herein, "O-Arm® 80"). The O-Arm® 80 can include, briefly, an emitting portion 82 and a receiving or imaging portion 84. The emitting portion 82 can emit any appropriate radiation, such as X-ray radiation, to allow acquisition of image data of the patient 14 when the patient 14 is positioned relative to the O-Arm® 80. The O-Arm® 80 includes a casing or housing system 86 that can house and enclose the emitting portion 82 in the imaging portion 84. Associated with the housing 86 can be a control panel or system 88. Alternative, or in addition thereto, the workstation 28 control the O-Arm® 80. The O-Arm® control system 88 can be similar to the C-Arm control system 26, such as initially acquiring and transmitting image data to the workstation 28, controlling the movement of the emitter 82 and the imaging portion 84, or any appropriate portions. It will be understood, however, that providing the separate control system 88 is not necessary.

The emitter portion 82 and the imaging portion 84 can be tightly controlled within the housing 86 relative to the patient 14, in part by moving on a track 90. In other words, the position of the emitter 82 and the imaging portion 84 can be substantially precisely monitored or determined and controlled relative to the patient 14 during the acquisition of image data of the patient 14. The position of the emitter portion 82 and the imaging portion 84 can be determined with switches, motion detection, internal tracking devices, transducers, etc. Also, a tracking device 34c can be interconnected with the O-Arm® 80. In addition, the theater in which the O-Arm® 80 is placed can be registered in the space to the O-Arm® 80. Thus, a physical location of a member relative to the O-Arm® 80 can be determined based upon the earlier registration. Therefore, one or more systems can be used to precisely determine the position of the O-Arm® 80 or portions thereof.

As one skilled in the art will understand regarding the O-Arm® 80, the O-Arm® 80 can position the emitter 82 and the imaging portion 84 relative to the patient 14, move the emitter 82 and the imaging portion 84, and then return the emitting portion 82 and the imaging portion 84 to the same previous position within about 0.2 mm to about 1.0 mm. This allows the O-Arm® 80 to be substantially precisely positioned relative to the patient 14.

The substantially precise knowledge or determination of the position of the imaging device relative to the patient 14 allows for substantially precise determination of the position of the orientation of the image data which can be correlated to a position of the patient 14. As one skilled in the art will understand, the image data of the patient acquired with the imaging system, such as the O-Arm® 80, can provide substantially different image data depending upon an orientation of the imaging portion, such as the imaging portion 84, relative to the patient 14. Therefore, substantially precise determination of the imaging portion relative to the patient 14 can be used to determine the orientation of the patient 14. For example, a medial-to-lateral or anterior-to-posterior image of the patient can be acquired. Substantially precisely determining the position of the O-Arm® 80 can be used to orient the image data obtained or acquired with the O-Arm® 80, even if not perfectly relative to the selected plane of the patient 14. It will also be understood, however, that the precise position of the O-Arm® 80 can be used to correlate the acquired intraoperative image data with preoperative image data. The correlation of the intraoperative image data and the preoperative image data can be used to register the patient 14 to the preoperative image data, as discussed further herein.

The O-Arm® 80 can also include various portions, such as a transport and base section that is operable to rest on a floor for support relative to the patient 14. The housing 86 can also maintain or enclose the track 90 on which the emitting portion 82 and the imaging portion 84 can be moved. The patient 14 can rest on an operating room table 92 that can also include base for positioning relative to the floor and the O-Arm® 80. The patient 14 can also be secured with a securing mechanism 94 to the operating table 92. The securing mechanism 94 can include a lockable strap, a Velcro® strap, a head frame (e.g. a Mayfield® head clamp), or any other appropriate holding mechanism. The patient holding or immobilization mechanism 94 can assist in holding the patient relative to the operating room table 92 and relative to the O-Arm® 80 so that the patient is imaged in a substantially fixed position relative to the O-Arm® 80. The emitting section 82 can emit selected radiation, such as X-ray radiation, along a beam line X' to the imaging or receiving section 84.

The position of the O-Arm® 80 or particular portions, such as the imaging section or receiving section 84 can be precisely determined. The position can be based only upon the movements of the imaging section 82 on the track 90. Alternatively, a tracking device 34c can also be interconnected with the O-Arm® 90. The tracking device 34c can be tracked with the tracking system 46 if the tracking device 34c is an electromagnetic tracking device. It will be understood that any appropriate tracking device can also be interconnected with the O-Arm® 80, such as an optical tracking device, a radio frequency tracking device, an acoustic tracking device, or any other appropriate tracking device. Nevertheless, the position of the O-Arm® 80 and the physical space can be determined.

According to various embodiments, the precise determination of the receiving section relative to the patient 14 can be used to determine the orientation of the image data acquired in the imaging section 84 from the patient 14. The precise position of the imaging section 84 can be used to determine the appropriate orientation and position of the patient 14 from the transmission of the X-rays along the beam line X'. If the patient 14 is substantially fixed relative to the O-Arm® 80, the tracking device 34c interconnected with the O-Arm® 80 may not be necessary. The O-Arm® 80, as it acquires image data of the patient 14, remains substantially fixed relative to the patient 14. Therefore, the image data acquired of the patient 14 with the O-Arm® 80 is acquired from a substantially known position relative to the patient 14 and this can be used to define the position of the patient 14, as discussed further herein.

The O-Arm® 80 can also image the fiducial marker 58 interconnected with the patient 14, if selected. Alternatively, the O-Arm® 80 can image the patient 14 alone without additional fiducial markers 58 interconnected with the patient 14. According to various embodiments, the landmarks of the patient 14 or the fiducial markers 58 can produce image data fiducial points. As discussed above, the image data fiducial points can simply refer to those portions of the image data that can be used to register the image data to other image data or the physical space.

As discussed further herein, the intraoperative image data acquired with the various imaging systems, including the O-Arm® 80 or the C-Arm 18 can be used to register the preoperative acquired image data. It will be understood, however, that the imaging system can be a preoperative imaging system or an intraoperative imaging system, only the timing of the acquisition of the image data is different. As discussed herein, the registration of the intraoperative image data to the preoperative image data can be used to register the patient 14 to the preoperative image data. Therefore, the determination of the position of the imaging device, including the O-Arm® 80 and the C-Arm 18, can be used to register the patient 14 and the patient space to the image space of the image data. Various other imaging devices can also be used in a substantially similar manner. For example, an intraoperative MRI system 120 can be used to acquire intraoperative image data of the patient 14.

The intraoperative MRI imaging system 120, with reference to FIG. 3, can include any appropriate system, such as the PoleStar® imaging system sold by Medtronic Inc. The intraoperative MRI imaging system 120 can include selected portions, such as those generally understood by one skilled in the art. In brief, the portions of the intraoperative MRI imaging system 120 can include a first magnet 122 and a second magnet 124. The two magnets 122, 124 can be permanent magnets, electromagnets, or a combination thereof. It will also be understood that various transmission portions, such as an RF transmission portion, can be incorporated into the intraoperative MRI imaging system 120. The various portions of the intraoperative MRI imaging system 120, including the magnets 122, 124 can be held or carried by a frame structure 126. A frame structure 126 can allow movement of the magnets 122, 124 relative to the patient 14.

The patient 14 can be positioned on a bed 128 that can be designed for use with the intraoperative MRI imaging system 120. It will be understood that a specific bed, however, is not required and any appropriate system can be used. Nevertheless, the intraoperative MRI imaging system 120 can be used with the bed 128 that includes a recess or small portion 130 near the region of the patient to be imaged, such as the cranium 60 of the patient 14. The cranium 60 of the patient can be positioned between the two magnets 122, 124 and the cranium 60 of the patient 14 can be imaged.

Similar to the O-Arm® 80 or the C-Arm 18, the patient 14 can be fixed relative to the imaging system 120. For example, the operating bed 128 can be fixed to the floor of the operating room as can the frame 126 of the intraoperative MRI imaging system 120. Further, the patient 14 can be fixed to operating room bed 128 with the patient restraining portion or member 94, which can be similar to the restraining portion 94 in use with the O-Arm® 80. The restraining portion can restrain a torso, appendage, a cranium, or any appropriate portion of the patient 14. Further, various bone fixation or securing portions can be used such as a head clamp (e.g. Mayfield ® head clamp).

The intraoperative imaging system 120 can also include a control portion 132. The control portion 132 includes a control portion similar to the control portion 88 of the O-Arm® 80 or the control portion 26 of the C-Arm 18. The control portion can include a separate processor, user input, display or output portion, or any appropriate portion to assist in controlling the intraoperative MRI imaging system 120. The intraoperative MRI imaging system controller 132 can be interconnected with the work station 28. Alternatively, the controller 132 can be incorporated into the work station 28 to control the intraoperative imaging system 120. Further, image data acquired with the intraoperative MRI imaging system 120 can be controlled or first stored in the controller 132 then transported to the work station 28 or can be transferred immediately to the work station 28.

The intraoperative MRI imaging system 120 can image the patient 14 using a generally understood MRI imaging techniques. Nevertheless, the position of the portions of the intraoperative MRI imaging system 120 relative to the patient 14 can be used to determine the orientation of the patient 14 and position of the patient 14 in physical space or define a physical space. Therefore, according to various embodiments, a tracking device 34d can be interconnected with the intraoperative MRI imaging system 120. The tracking device 34d can be used in the tracking system 46 to determine a position of the intraoperative MRI imaging system 120 in a physical space. It will be understood that the tracking device 34d can be any appropriate tracking device, such as an electromagnetic tracking device, an optical tracking device, an acoustic tracking system, a radio frequency tracking system, or any appropriate tracking system. For example, an optical tracking device 34d' can be used with an optical localizer 46'. An optical DRF 44' can also be used with the optical localizer.

Further, the patient 14 can have the fiducial markers 58 interconnected with the patient 14. The fiducial markers 58 can be imaged with the intraoperative MRI imaging system 120, including the markers sold by IZI Medical Products of Baltimore, Md. The markers can be imaged with the intraoperative MRI imaging system 120 to create image data fiducial points. Alternatively, as discussed above, various landmarks can be used to create image data fiducial points.

The intraoperative imaging system 120 can include various imaging resolutions or powers. For example, the intraoperative MRI imaging system can be about 0.1 Tesla to about 5.0 Tesla, including about 0.1 to about 1.0 Tesla. Differing strengths of the intraoperative MRI imaging system 120 can assist in creating differing resolutions of the image data acquired of the patient 14. Therefore, it will be understood, that the landmarks of the patient 14 can be used at various resolutions for registration of the intraoperative image data acquired of the patient 14 while other resolutions can use the image data fiducial points created by the fiducial markers 58. It will be understood, however, that any appropriate resolution can be used for the registration, via the fiducial markers 58 or the landmarks of the patient 14.

According to various embodiments, the optional DRF 44 can be attached to the patient 14 in conjunction with any of the imaging systems in the navigation system 10. The DRF 44 can be optionally attached to the patient 14 to assist in tracking the patient 14 in physical space. Again, the optional dynamic reference frame 44 can be interconnected with the patient 14, according to various embodiments, but may not be required.

As discussed above, various embodiments including the intraoperative imaging system can be used to acquire image data of the patient 14 during an operative procedure. Again, as discussed above, the intraoperative image data acquired of the patient 14 need not be acquired of the patient 14 after an incision is formed on the patient 14, or at any particular time. The intraoperative image data is acquired after preoperative image data is acquired and can be used to assist in registering the image space to physical space. The process of registering the image space from the preoperative image data to the physical space of the patient in the operating room is discussed further herein. Moreover, it will be understood that although the exemplary processes are related to a cranial procedure, registration can occur relative to any appropriate portion of the anatomy, such as an arm, a leg, a spine, or the like. Moreover, the registration can occur at any appropriate time and need not be during an operative procedure, but can be during any appropriate procedure.

Figure 4:
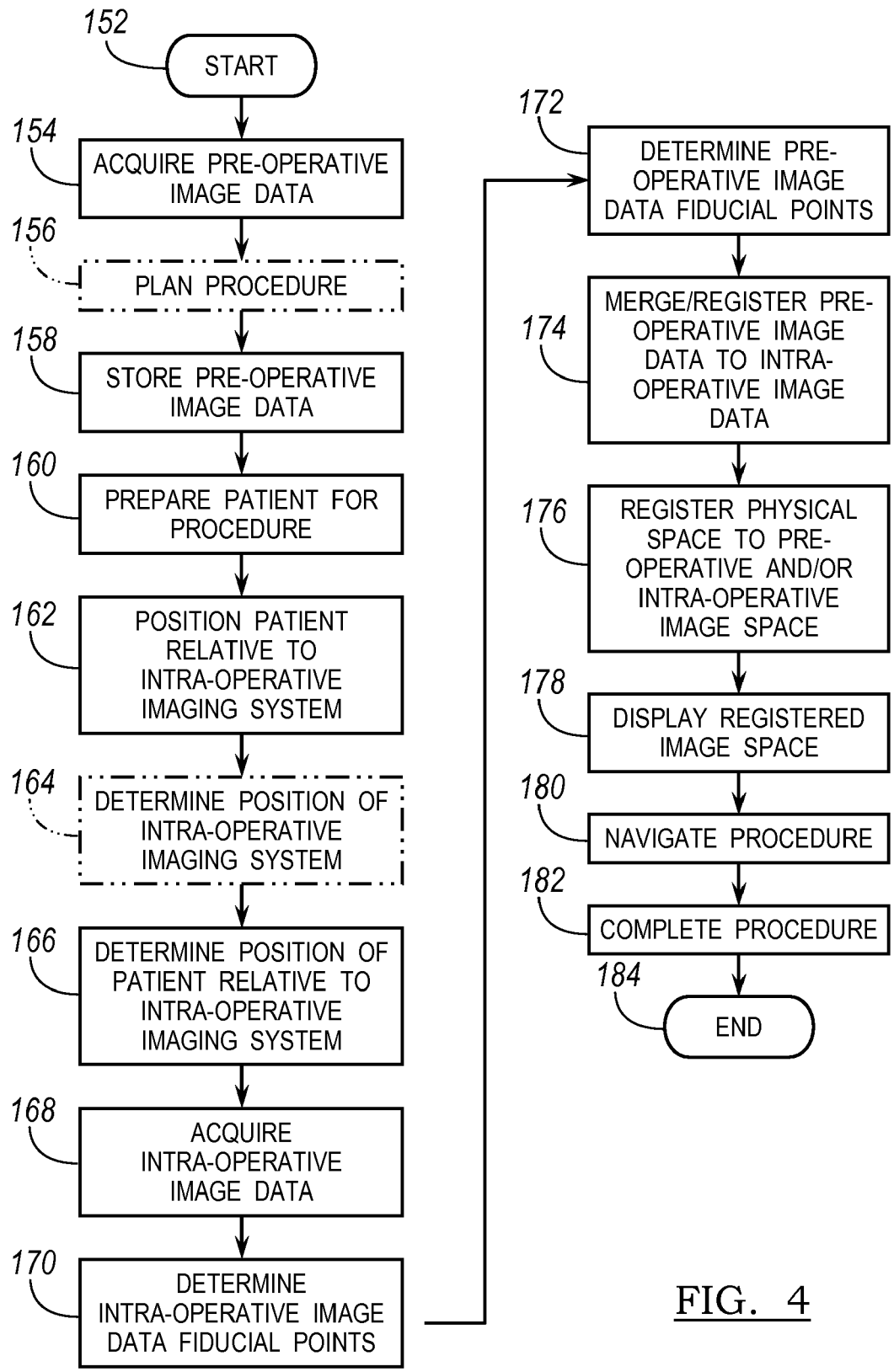
FIG. 4 is a flow diagram of a procedure for registering image space to patient space, according to various embodiments.

With reference to FIG. 4, a procedure for registration of image space to patient space 150, is illustrated. The registration procedure 150 can include various portions, as discussed in detail herein, including registration or merging of intraoperative image data to preoperative image data and using or utilizing the merging of the intraoperative to preoperative image data to register image space to patient space. As discussed herein, the registration procedure 150 can make use of both preoperative image data and intraoperative image data. Both the preoperative image data and the intraoperative image data can define image space. Therefore, the preoperative image data can define preoperative image space and the intraoperative image data can define intraoperative image space. Further, both the intraoperative image data and the preoperative image data can include image data fiducial points. Therefore, the preoperative image data can include preoperative image data fiducial points and the intraoperative image data can include intraoperative image data fiducial points. Moreover, although the registration procedure can register preoperative image data to patient space or physical space, the intraoperative image data can also be registered to the physical space or patient space, either inherently or via registration techniques understood by one skilled in the art.

The registration procedure 150 can be carried out, at least in part, in a processor, such as a processor in various portions of the navigation system 10. For example, the processor within the workstation 28 can process the image data and various algorithms to register image data to image data, such as preoperative image data to intraoperative image data. It will be understood therefore, that the registration process 150 can be understood to be substantially an automatic registration process even though the user 60 may intervene, such as positioning the patient 14 relative to the intraoperative imaging system 16, 80, 120.

The registration procedure 150 can start at start block 152. Preoperative image data can then be acquired in block 154. Acquiring a preoperative image data can include any appropriate imaging technique. For example, CT image data can be acquired, MRI image data can be acquired, ultrasound image data can be acquired, or any other appropriate image data type or combinations of image data types. The preoperative image data can include the three dimensional image data, two dimensional image data, four dimensional image data, or combinations of dimensional image data. The image data acquired preoperatively can be formed into a 3-D model from 2-D slices, maintained as 2-D slices, or be acquired as a three dimensional model. Further, the preoperative image data acquired in block 154 can be morphed or augmented by atlas or patient model data. Thus, the image data acquired in the acquired preoperative image data block 154 can be image data purely from the patient 14 or be augmented or fit to models for various diagnostic and treatment techniques.

Once the preoperative image data is acquired in the acquired preoperative image data block 154, a procedure can be optionally planned in planning procedure block 156. Planning a procedure is not required for the registration procedure 150 and can be carried out in various embodiments for use by the user 60, during or prior to the operative procedure. Nevertheless, planning a procedure in planning procedure block 156 can assist in performing a procedure on the patient 14. Planning can include determining various optimal or selected trajectories of implants, final positions of implants, therapies to be applied to the patient, diagnosis of the patient 14, or other purposes. The implants can include various members, such as one or more deep brain stimulation leads, one or more micro-electrode leads, etc. Therefore, the planning procedure block 156 is optional and illustrated merely for exemplary purposes.

The acquisition of the image data in block 154 or the planning in block 156 can include determining preoperative image data fiducial points. The preoperative image data fiducial points can include any appropriate fiducial point. Also, one skilled in the art will understand that the preoperative image data fiducial points can include a single point, a plurality of points, a surface, or a surface defined by a plurality of points. Therefore, the image data fiducial point may not only be a single point (e.g. a pixel or a voxel), but can include a plurality of points that define a region.

For example, the patient 14 can be imaged with the fiducial markers 58. Therefore, the identification in the preoperative image data fiducial points can include identifying the points in the image data where the image marker 58 was imaged. According to various embodiments, the preoperative image data fiducial point can also include the identification of surfaces in the preoperative image data. Either a computer algorithm, the user 60, or a combination thereof can be used to identify the fiducial points in the image data including surfaces within the preoperative image data.

Subsequent to the acquisition of the preoperative image data in block 154 or the planning procedure block 156 the preoperative image data can be stored in storage block 158. The stored preoperative image data can be only the image data of the patient, or can include other information. For example, the stored preoperative image data from block 158 can include image data morphed to a model, additional atlas data from an atlas data model, or planning information, such as trajectories, therapy types, or the like. The storage of the image data in storage block 158 can be stored in any appropriate system, such as a memory system of the workstation 28. The workstation 28 can then be used to display the preoperative image data on the display 36 as the image data 38. It will be understood, however, that any appropriate data can be displayed on the display 36 and the stored preoperative image data is merely exemplary.

After the storing of the preoperative image data in block 158, the patient 14 can then be prepared for a procedure in block 160. The preparation of the patient 14 for the procedure in block 160 can be any appropriate preparation. For example, the patient can have the dynamic reference frame 44 attached to the patient 14, the fiducial marker 58 reattached or maintained relative to the patient 14, or any appropriate preparation steps.

The patient 14 can then be positioned relative to the selected intraoperative imaging system in the positioning block 162. The positioning of the patient in block 162 can include moving the patient relative to the intraoperative imaging system 18, 80, 120, fixing the patient 14 relative to the intraoperative imaging system, or any appropriate positioning procedure. For example, as discussed above, the patient 14 can be fixed relative to the intraoperative imaging system with the patient fixation device 94, according to various techniques. Nevertheless, positioning of the patient 14 relative to the intraoperative imaging system can assist in fixing the patient 14 relative to the intraoperative imaging system. Moreover, as discussed above, the patient 14 need not be substantially fixed relative to the intraoperative imaging system and fixing the patient relative to the intraoperative imaging system is merely exemplary. In any instance, the patient 14 can be positioned relative to the intraoperative imaging system to allow for imaging of the patient 14.

The registration process 150 can then determine the position of the intraoperative imaging system in block 164. Although determining the position of the intraoperative imaging system in block 164 is exemplary and not required, as discussed above, the tracking device 34, 34c, and 34d can be used to track or determine a position of the intraoperative imaging system in the physical space. According to various embodiments, the position of the intraoperative imaging system can be used to correlate the image data obtained or acquired with the intraoperative imaging system to a position in physical space. According to various embodiments, however, the intraoperative imaging system can be fixed relative to the patient and be used to define the intraoperative physical space. Therefore, determining a position of the intraoperative imaging system is not required and can be used according to various embodiments.

The position of the patient relative to the intraoperative imaging system can be determined in determination block 166. The position of the patient in block 166 can be determined using the DRF 44 interconnected with the patient 14. The determination of the position of the patient in block 166 can be performed using various techniques, such as with the tracking systems 46, 46' or any appropriate tracking system. The position of the patient 14 in physical space can be tracked or determined with the tracking system, and that position can be used to register to the preoperative image space, as discussed further herein.

Once the patient has been positioned in block 162, the optional determination of the position of the intraoperative imaging device has occurred in block 164, and the position of the patient is determined in block 166, acquisition of intraoperative image data can be in acquisition block 168. The acquired intraoperative image data in block 168 can be any appropriate type of intraoperative image data, including those discussed above. The acquisition of the intraoperative image data in block 168 can occur according to any appropriate mechanism, such as user initiated image data acquisition. Although preoperative image data and intraoperative image data can both be acquired of the patient 14 both create image data of the patient 14. Thus, image data can simply be image data unless otherwise indicated.

Once the intraoperative image data is acquired from the intraoperative imaging system, the determination or a determination of intraoperative image data fiducial points can be determined in block 170. The determination of the intraoperative image data fiducial points can be substantially similar to the determination of the preoperative image data points, which can optionally occur in block 172. As discussed above, the determination of the preoperative image data fiducial points can occur immediately after the acquisition of the preoperative image data or at any appropriate time. Also, the determination of the intraoperative image data fiducial points and the preoperative image data fiducial points can be substantially similar and occur substantially simultaneously.

According to various embodiments, the patient 14 can be imaged with the intraoperative imaging system with the fiducial marker 58 attached to the patient 14. Therefore, the intraoperative image data can include image data produced by the fiducial markers 58. The image data fiducial points from the intraoperative or preoperative image data can then be determined as the points defined by the fiducial marker 58.

In addition, a plurality of points, a surface, or the like can be determined in the intraoperative image data to produce the intraoperative image data fiducial points. For example, the cranium 60 of the patient 14 can include various distinct surfaces, such as the orbits, the brow ridge, nose bridge, etc. These distinct surfaces can appear or be recognized in selected image data. Various computer algorithms (e.g. boundary or edge recognition, region growing, etc.) or user intervention can occur to determine the surfaces and their location. Matching these surfaces or correlating them in various image data sets can allow for merging or correlation of different image data sets, such as preoperative image data sets and intraoperative image data sets.

Preoperative image data fiducial points can be determined in a substantially similar manner as intraoperative image data fiducial points. Both can be based on surfaces, points, etc. Each of the types of fiducial points can be used to merge, register, and/or correlate the intraoperative image data and the preoperative image data. Again, the preoperative image data fiducial points can be determined preoperatively or intraoperatively.

Once the intraoperative image data fiducial points are determined in determination block 170 and the preoperative image data fiducial points have been determined in block 172, a merge or registration of the preoperative image data to the intraoperative image data can occur in block 174. The merging of the intraoperative image data to the preoperative image data can occur using various generally known techniques. For example, surface matching algorithms can be used to merge or register the intraoperative image data to the preoperative image data using the fiducial points identified in each image data set. Further, various point registration techniques can be used to merge or register the intraoperative image data and the preoperative image data. The merging or registration of the intraoperative image data and the preoperative image data can be performed with a processor, such as the processor within the workstation 28. It will be understood, however, that any appropriate processor or processor system can be used to register the intraoperative image data and the preoperative image data.

The registration or merging of the preoperative image data to the intraoperative image data can allow for the creation of a registration map or correlation of each of the points in the preoperative image space to the intraoperative image space. The correlation of the preoperative image data to the intraoperative image data can allow for a registration of the physical space to the preoperative image data and/or the intraoperative image in block 176.

The registration of the physical space to the image space, either in the preoperative image data or the intraoperative image data, can occur according to various generally known techniques. Once the intraoperative image data and the preoperative image data are merged or registered, the determined or known position of the intraoperative imaging system can be used to determine the position of the patient 14 within the physical space. The position of the patient in the intraoperative image data can be used to define the patient space. Thus, the registration of the intraoperative image data to the preoperative image data registers the preoperative image space to the patient space. Again, this can be performed substantially with a processor, allowing for a substantial automatic registration of the preoperative image data to the physical space.

According to various embodiments, the position of the intraoperative imaging system and the position of the patient can also be tracked with the various tracking devices, such as the tracking device 34 and the DRF 44. This can allow the position of the intraoperative imaging system to be determined during the acquisition of the image data intraoperatively. Therefore, the image data acquired of the patient 14 during the intraoperative imaging can be merged to the preoperative image data to define or register the preoperative image space to the physical space of the patient 14. By determining or knowing the position of the patient 14 and the position of the intraoperative imaging device during the imaging, the registration of the intraoperative image data to the preoperative image data can be used to register the preoperative image data to the physical space.

Various systems can be used in the registration. Point registration can use fiducial markers 58 attached to the patient. Surface matching algorithms can use surface or edge finding algorithms in the image data. Further, surfaces of the patient 14 can be determined in physical space with the intraoperative image data and surface or edge determining algorithms can be used to determine surfaces in the intraoperative image data. Thus, it will be understood, that the registration of physical space to the preoperative image space can occur with fiducial markers on the patient 14, without fiducial markers on the patient 14, while the patient is fixed relative to the imaging system or while the patient is not fixed relative to the imaging system.

Regardless, the intraoperative imaging system can image the patient 14 to allow for the determination of intraoperative image data fiducial points. Although fiducial markers can be interconnected with the patient 14, during the intraoperative image data acquisition in block 168, the intraoperative image data acquisition allows the determination of the image data fiducial points without requiring the user 60 to identify fiducial points on the patient or in the image data. The intraoperative imaging system can acquire appropriate image data of the patient 14 to allow for determination of the intraoperative image data fiducial points substantially automatically with a processor system. Appropriate systems include the fiducial marker determination system disclosed in U.S. pat. app. Ser. No. 11/693,558 (unofficial) (Attorney Docket No. 5074A-000102), filed on Mar. 29, 2007 (unofficial), incorporated herein by reference.

In summary, the intraoperative image data can define, at least in part, the physical space. The intraoperative image data is acquired from an intraoperative imaging system that has a known position relative to the patient 14. The known position can be based upon fixing the patient 14 relative to the intraoperative imaging system or by tracking both the patient 14 and the intraoperative imaging system. According to various embodiments, therefore, the intraoperative image data defines the physical space. Thus, the correlation or merging of the intraoperative image data with the preoperative image data allows the preoperative image data to be registered to the physical space. As discussed herein, this can allow navigation relative to the preoperative image data.

The image space can be defined by the preoperative image data, the intraoperative image data, or combinations thereof. Once the physical space has been registered to the image space, a display of the image data can be displayed on the display 36 in display block 178. It will be understood, however, that registration of the image space to physical space can be to both the intraoperative image data and the preoperative image data. Moreover, both can be displayed on the display device 36. The display of the image data in block 178 can allow for a procedure to be navigated in block 180. As one skilled in the art will understand, an icon representing a position of an instrument, such as a catheter, a deep brain stimulation (DBS) lead, a micro-electrode (ME) lead, a catheter, an ablation catheter, or any other appropriate instrument can be displayed relative to the image data on the display 36. The display of the icon superimposed on the image data 38 can illustrate a position of the instrument in physical space relative to the patient 14.

One skilled in the art will understand that the processes and systems discussed above can be used in a surgical procedure. The processes and systems, however, are understood to not be limited to use during or with a surgical procedure. The systems and processes can be used to acquire information regarding inanimate objects, inform or build a database of information; plan a procedure; formulate teaching aids, etc. Registration of image space to physical space can be performed relative to any object in physical space, including a patient, an inanimate object, etc. Also, the registration can occur for any appropriate reason, which may or may not be a surgical procedure.

The procedure can then be completed in block 182 which can include any appropriate technique. For example, the therapy can be provided, the implant can be fixed in place, or any appropriate procedure can occur. The registration process can then be added in block 184.

The teachings herein are merely exemplary in nature and, thus, variations that do not depart from the gist of the teachings are intended to be within the scope of the teachings. Such variations are not to be regarded as a departure from the spirit and scope of the teachings.

What is claimed is:

1. A navigation system for registering an image space to a physical space relative to a patient for a surgical procedure, comprising:

a tracking system including a localizer and a tracking device;

a system operable to access intraoperative image data of the patient that was acquired at a determined position relative to the patient in the physical space;

a processor operable to at least one of determine a position of the tracking device in the physical space, determine an intraoperative image data fiducial point in the intraoperative image data, determine a preoperative image data fiducial point in a preoperative image data, correlate the intraoperative image data and the preoperative image data with the intraoperative image data fiducial point and the preoperative image data fiducial point, or combinations thereof;

wherein the preoperative image data is operable to be registered to the physical space to correlate points in the preoperative image data with corresponding points in the physical space based upon the intraoperative image data that was acquired at the determined position relative to the patient;

wherein the registered preoperative image data allow navigation of the tracking device in the physical space relative to the preoperative image data;

wherein the processor is operable to determine the position of an intraoperative imaging system to determine a position relative to the determined intraoperative fiducial image data point in the physical space.

2. The system of claim 1, further comprising:
a preoperative imaging system operable to acquire the preoperative image data of the patient; and
an intraoperative imaging system operable to acquire the intraoperative image data of the patient.

3. The system of claim 2, wherein the intraoperative imaging system and the preoperative imaging system are a single imaging system.

4. The system of claim 1, further comprising:
a display device operable to display at least one of the intraoperative image data, the preoperative image data, or combinations thereof.

5. The system of claim 4, further comprising:
an instrument, wherein the tracking device is operable to track an instrument position.

6. The system of claim 5, wherein the instrument is at least one of a deep brain stimulation electrode, a micro-electrode, a catheter, an ablation catheter, or combinations thereof.

7. The system of claim 4, wherein the display device is operable to display an icon representing an instrument superimposed on the registered preoperative image data for the navigation of the tracking device.

8. The system of claim 1, further comprising:
a fiducial marker operable to be imaged and form the intraoperative image data fiducial point and the preoperative image data fiducial point.

9. The system of claim 1, further comprising:
a second processor operable to at least one of determine a position of the tracking device in the physical space, determine an intraoperative image data fiducial point in the intraoperative image data, determine a preoperative image data fiducial point in a preoperative image data, correlate the intraoperative image data and the preoperative image data with the intraoperative image data fiducial point and the preoperative image data fiducial point, or combinations thereof.

10. The system of claim 1, wherein the processor is operable with the determination in the physical space to register the preoperative image data and the physical space.

11. The system of claim 10,
wherein the determined position of the intraoperative imaging system relative to the patient in the physical space is based on tracking the intraoperative imaging system;
wherein the intraoperative image data is acquired with the intraoperative imaging system and defines at least a portion of the physical space;
wherein the preoperative image data is correlated to the intraoperative image data to be registered to the physical space with the processor.

12. The system of claim 1, wherein the intraoperative imaging system is at least one of a computed tomography imaging system, a magnetic resonance imaging system, an ultrasound imaging system, an X-ray imaging system, or combinations thereof.

13. A method of registering an image space to a physical space relative to a patient, comprising:
accessing preoperative image data of the patient;
determining a preoperative image data fiducial point in the preoperative image data;
accessing intraoperative image data of the patient, wherein the intraoperative image data defines at least a portion of the physical space;
determining an intraoperative image data fiducial point in the intraoperative image data;
correlating the preoperative image data and the intraoperative image data using the determined preoperative image data fiducial point in the preoperative image data and the determined intraoperative image data fiducial point in the intraoperative image data;
accessing a determined position of an intraoperative imaging system that acquired the intraoperative image data to determine a position of the patient within the physical space; and
correlating the correlated preoperative image data to the physical space based at least on the accessed determined position of the intraoperative imaging system.

14. The method of claim 13, further comprising:
determining the position of the intraoperative imaging system relative to the patient such that acquiring intraoperative image data includes acquiring image data of the physical space including the patient.

15. The method of 14, further comprising:
fixing the patient relative to an intraoperative imaging system that acquires the intraoperative image data.

16. The method of claim 15, wherein correlating the preoperative image data and the intraoperative image data includes:
processing the intraoperative image data with an intraoperative image data processor to determine the intraoperative image data fiducial point; and
processing the preoperative image data with a preoperative image data processor to determine the preoperative image data fiducial point.

17. The method of claim 16, wherein the intraoperative image data processor and the preoperative image data processor are the same processor.

18. The method of claim 16, wherein the intraoperative image data fiducial point and the preoperative image data fiducial point are the same type of fiducial point.

19. The method of claim 16, wherein each of the intraoperative image data fiducial point and the preoperative image data fiducial point is a surface, a single point, a pixel, a voxel, a marker, or combinations thereof.

20. The method of claim 13, wherein correlating the correlated preoperative image data includes:
tracking an imaging device;
acquiring the intraoperative image data with the imaging device;
defining the physical space with the intraoperative image data; and
registering the preoperative image data to the physical space.

21. The method of claim 13, wherein each of the determined preoperative image data fiducial point in the preoperative image data and the determined intraoperative image data fiducial point in the intraoperative image data include:
attaching a fiducial marker to the patient; and
imaging the fiducial marker and the patient;
wherein the preoperative image data of the fiducial marker defines the preoperative image data fiducial point and the intraoperative image data of the fiducial marker defines the intraoperative image data fiducial point.

22. The method of claim 13, further comprising:
moving the patient relative to the intraoperative imaging system;
wherein acquiring the intraoperative image data of the patient occurs subsequent to the acquisition of the preoperative image data.

23. The method of claim 13, further comprising:
planning a procedure for the patient with the preoperative image data.

24. The method of claim 13, further comprising:
navigating an instrument relative to the patient in the physical space;
wherein the correlated preoperative image data to the physical space includes registering the image space to the physical space;
wherein the image space is defined by at least one of the intraoperative image data, the preoperative image data, or combinations thereof.

25. A method of registering an image space to a physical space relative to a patient, comprising:
accessing a first image data set of the patient;
determining a first image data set fiducial point;
preparing the patient for a surgical procedure in at least a portion of the physical space;
defining at least a portion of the physical space in a second image data set of the patient including at least determining a position of the patient in the second image data relative to a first imaging system;
determining a second image data set fiducial point;
correlating the first image data set and the second image data set at least in part by matching the first image data set fiducial point and the second image data set fiducial point; and
registering the first image data set with the physical space with the correlation of the first image data set and the second image data set, wherein the physical space includes a space in which the patient is positioned and the registration allows for navigation of a member within the physical space relative to the first image data.

26. The method of claim 25, further comprising:
navigating an instrument relative to the patient based upon the registration.

27. The method of claim 25, further comprising:
tracking a location of the first imaging system while the second image data set is acquired; and determining a position of the first imaging system in the physical space at least in part with the tracking a location of the first imaging system.

28. The method of claim 27, further comprising:
tracking a position of the patient during the acquisition of the second image data set; and
determining a position of at least a portion of the physical space based upon the tracked position of the patient.

29. The method of claim 27, further comprising:
fixing the patient in physical space relative to the first imaging system.

30. The method of claim 25, further comprising:
attaching a fiducial marker to the patient; and
acquiring the second image data set with the attached fiducial marker;
wherein determining the second image data set fiducial point includes determining a portion of the second image data set formed by imaging the fiducial marker.

31. The method of claim 30, further comprising:
acquiring the first image data set with the fiducial marker attached to the patient;
wherein determining the first image data set fiducial point includes determining a portion of the second image data set formed by imaging the fiducial marker.

32. The method of claim 25, further comprising:
acquiring the first image data set prior to moving the patient into an operating theater.

33. The method of claim 25, further comprising:
acquiring the second set of image data after moving the patient into an operating theater.

34. The method of claim 25, wherein the first image data set defines a first image space of the patient;
wherein the second image data set defines a second image space of the patient and at least defines a portion of the physical space.

35. The method of claim 25, wherein navigating a procedure includes navigating a deep brain stimulation electrode, navigating a micro-electrode, navigating a catheter, navigating an ablation catheter, or combinations thereof.

36. The method of claim 25, further comprising:
determining a position of an imaging system in the physical space;
acquiring the second set of image data; and
defining at least a portion of the physical space with the second set of image data;
wherein the defining at least a portion of the physical space with the second set of image data includes determining the position of the patient relative to the imaging system while the second image data set is acquired.

37. The method of claim 25, wherein determining the first image data set fiducial point, determining the second image data set fiducial point, or combinations thereof include at least one of determining in each of the first image data set and the second image data set a pixel, a voxel, a surface, a region, or combinations thereof.

38. The system of claim 1, wherein the patient is moved from the preoperative imaging system to the intraoperative imaging system.

* * * * *